United States Patent
Bert et al.

(10) Patent No.: US 7,928,415 B2
(45) Date of Patent: Apr. 19, 2011

(54) DEVICE FOR IRRADIATING TUMOUR TISSUE IN A PATIENT WITH A PARTICLE BEAM

(75) Inventors: Christoph Bert, Aschaffenburg (DE); Eike Rietzel, Darmstadt (DE); Gerhard Kraft, Darmstadt (DE)

(73) Assignee: Gesellschaft für Schwerionenforschung mbH, Darmstadt (DE)

( * ) Notice: Subject to any disclaimer, the term of this patent is extended or adjusted under 35 U.S.C. 154(b) by 227 days.

(21) Appl. No.: 12/086,940

(22) PCT Filed: Dec. 8, 2006

(86) PCT No.: PCT/EP2006/011799
§ 371 (c)(1), (2), (4) Date: Dec. 22, 2008

(87) PCT Pub. No.: WO2007/079854
PCT Pub. Date: Jul. 19, 2007

(65) Prior Publication Data
US 2009/0095921 A1    Apr. 16, 2009

(30) Foreign Application Priority Data

Dec. 22, 2005   (DE) ................. 10 2005 063 220
Sep. 14, 2006   (DE) ................. 10 2006 043 066

(51) Int. Cl.
*A61N 5/00*    (2006.01)
(52) U.S. Cl. .................................... 250/492.3
(58) Field of Classification Search ............... 250/492.3; 607/1, 2
See application file for complete search history.

(56) References Cited

U.S. PATENT DOCUMENTS
6,710,362 B2 *  3/2004  Kraft et al. ............. 250/492.3
(Continued)

FOREIGN PATENT DOCUMENTS
DE       199 07 098       8/2000
(Continued)

OTHER PUBLICATIONS

J. Loef et al., "An adaptive control algorithm for optimization of intensity modulated radiotherapy considering uncertainties in beam profiles, patient set-up and internal organ motion" Phys. Med. Biol, vol. 43, pp. 1605-1628 (1998).

(Continued)

*Primary Examiner* — Kiet T Nguyen
(74) *Attorney, Agent, or Firm* — Peter F. Corless; Christine C. O'Day; Edwards Angell Palmer & Dodge LLP

(57) ABSTRACT

There is proposed a device for the slice-by-slice irradiation of tumour tissue (3) in a patient using a particle beam, having—an accelerator (7) for generating a particle beam (5) with predetermined energy for each slice, —a raster scanning device (9), acting on the particle beam (5), for the slice-by-slice scanning of the tumour tissue (3), —a modulator (17) for modulating the energy of the particle beam (5), —a detection device (37) for the time-resolved detection of the position of the tumour tissue (3) and having—a first storage device for storing data relating to the tumour tissue (3), which were determined prior to the irradiation operation, and for releasing that data to the raster scanning device (9) and to the modulator (17). The device is characterized by—a module (39), which registers the data on the course of the irradiation and the data of the detection device (37) which have been obtained during an irradiation operation.

3 Claims, 2 Drawing Sheets

Figure 1:
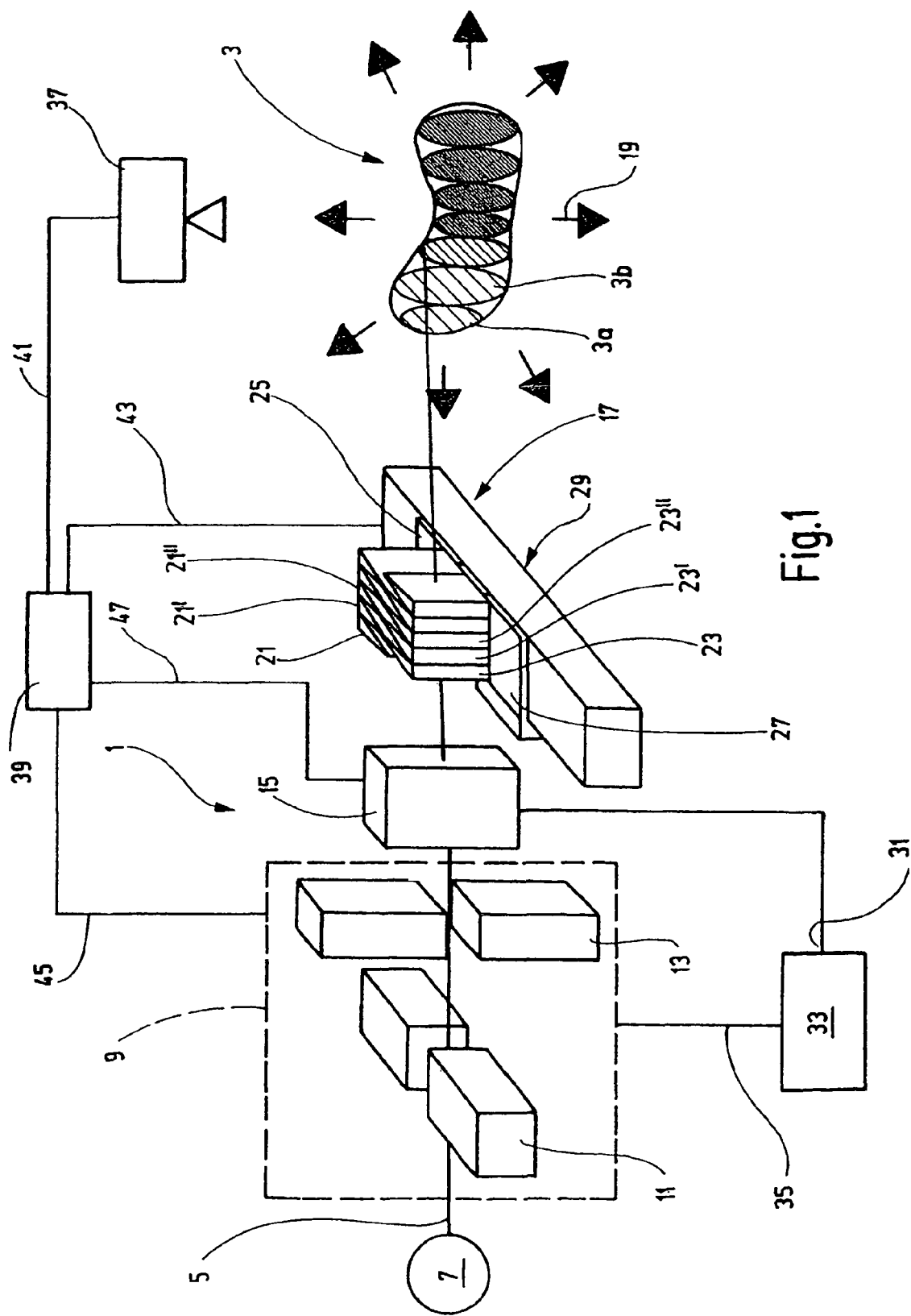

U.S. PATENT DOCUMENTS 6,799,068 B1 * 9/2004 Hartmann et al. ............... 607/2

FOREIGN PATENT DOCUMENTS

| DE | 100 31 074 | 1/2002 |
| EP | 1 121 947 | 8/2001 |
| WO | WO-2005/120641 | 12/2005 |

OTHER PUBLICATIONS

S.O. Groetzinger et al., "Volume Conformal Irradiation of Moving Target Volumes with Scanned Ion Beams", Vom Fachbereich Physik der Technischen Universitat Darmstadt, Chapters 2, 4 & 5 (2004).

* cited by examiner

DEVICE FOR IRRADIATING TUMOUR TISSUE IN A PATIENT WITH A PARTICLE BEAM

The invention relates to a device for the irradiation of patients, especially of tumour tissue in a patient, using a particle beam. The invention relates also to a method of compensating for movements of a patient, or of the irradiated region of a patient, during an irradiation operation.

Devices of the kind claimed here are known. They are used to compensate for movement of the irradiated target area during the irradiation of tumour tissue in a patient. Movement of the tumour tissue being irradiated occurs especially during a patient's respiratory movements. In order to minimise the effect of respiratory movements on the dose deposition in the tumour, the target volume is usually increased, which may cause damage to the patient because healthy tissue is irradiated as well. This increases the probability of side effects. There are already proposals for reducing the dose applied to healthy tissue. One proposal, for example, is to reduce the range of movement of the tumour tissue to be irradiated by compressing the abdominal wall, thereby limiting the mobility of the patient's diaphragm. Another possibility is to replace natural breathing with a high-frequency artificial breathing (jet-ventilation). Finally, hyperoxic artificial respiration, in which the breathing can be halted for a period, may also be considered.

A further possibility is interrupted irradiation (gating), in which the patient breathes normally and the tumour is irradiated only during a particular time window within which the tumour tissue being irradiated is in the desired position. That procedure has the result that the duration of the irradiation operation is persistingly increased.

It is also possible for the dose of radiation to be applied not all at once but over a number of cycles. That repeated, irradiation (rescanning) requires an enlargement of the target volume. Enlargement of the target volume is necessary because the tumour needs to be irradiated in all states of movement. This can result in damage to the patient, because healthy tissue is irradiated as well. An average of the interferences is taken, as described below, in order to achieve the desired dose-loading of the tumour. In that method, it is necessary for the tumour to be hit in all states of movement, resulting in unnecessary loading of healthy tissue. It has been found that, if the particle beam does not track a movement of the tumour tissue being irradiated then, compared with static irradiation, differences occur that adversely affect the result of the irradiation. In the tissue that is being irradiated, regions that are not irradiated, or that are irradiated more than once, result, because the progression of the irradiation and the movement of the tumour are superimposed on one another.

There is finally also known a device that is used to irradiate tumour tissue in which a control means is provided by means of which it is possible to compensate for a change in position of the tumour tissue during the irradiation operation (DE 10 31 071 A1). In that arrangement, it is necessary to determine the exact course of the irradiation operation in time correlation with the tumour movement in order to understand the dose applied.

The aim of the invention is accordingly to provide a device that allows a precise time correlation to be made between irradiation sequence and tumour movement.

To solve that problem, a device having the features mentioned in claim 1 is proposed. The device comprises the usual elements, namely an accelerator for generating a particle beam, referred to as the treatment beam, having a predetermined particle energy for each slice, and a raster scanning device, which deflects the particle beam in two directions that are perpendicular to each other and which renders possible slice-by-slice scanning of the tumour tissue. The device furthermore has a modulator, which is able to change the energy of the particle beam so that the region of maximum dose-loading predetermined by the acceleration energy, the so-called Bragg maximum of a particle beam, which occurs at different depths of the tumour tissue, can rapidly be changed in order to match the penetration depth to changes of the anatomy. A detection means of the device serves to detect the position of and displacements of the tumour tissue. It therefore renders possible a time-resolved detection of the position of the tumour tissue. The data obtained by the detection device are conveyed to a first storage device. In addition, the movement of the tumour, for example respiratory movement of a patient, as registered prior to the irradiation operation, can be stored in the storage device. The movement of the tumour, for example a patient's respiratory movements, is detected prior to an irradiation operation and stored in the storage device. In that way it is possible so to deflect the particle beam during an irradiation operation that it substantially follows the movement of the tumour tissue and the particular penetration depth required is adapted by way of the modulator.

The device according to the invention is distinguished by the fact that a module is provided that, on the one hand, registers data on the course of the irradiation. Accordingly, the positions of the particle beam predetermined by the raster scanning device are detected over time, and also the energy, provided by means of the accelerator for the irradiation, of the particle beam, including a possible modulation. It is therefore possible to determine at what depth the Bragg maximum of a particle beam lies.

On the other hand, the module registers data of a detection device used during the irradiation of a patient, which device detects over time the position of the tumour tissue being irradiated. In that arrangement it is possible for the position to be determined indirectly by means of a camera, for example by colour markers or light sources, especially light-emitting diodes, applied to the skin of the patient being irradiated, the movement of which is detected during an irradiation operation. Other possibilities might be direct fluoroscopic detection of the tumour position or detection of the surface movement of the patient.

The device is thus distinguished by the fact that, during an irradiation operation, exact information exists about the course of the irradiation and about the movement of the tumour tissue being irradiated. The inter-relationship between the course of the irradiation and the movement of the tumour tissue is registered by a correlation unit within the module. The data of the correlation unit gives information about which dosage is to be allocated to which tumour region or raster point.

Further developments are evident from the sub-claims.

This problem is also solved by a method, of compensating for movements of a patient, or of the irradiated region of the patient, during irradiation with a particle beam. In the method, the tumour tissue is irradiated taking into account data stored in a storage device. Those data have been obtained by means of a detection device during a detection operation connected in series before the actual irradiation operation, that device being used for the time-resolved detection of the position of tumour tissue, that is, the detection of movement of the tumour tissue.

During an irradiation operation, data on the course of the irradiation is registered in a module. The slice-by-slice scanning of the tumour tissue is thus detected by means of the raster scanning device and the energy of the particle beam.

During irradiation, in addition the current position of the tumour tissue over time is registered by the module. Then, by correlation of the data on the course of the irradiation and the data on the course of the movement, the association of the current tumour position with a current irradiation course is possible. The dose deposited in the tumour can thus be ascertained.

In connection with the operation of the device, there are used in solving the stated problem a method of dose calculation and/or a method of irradiation planning.

Figure 2:
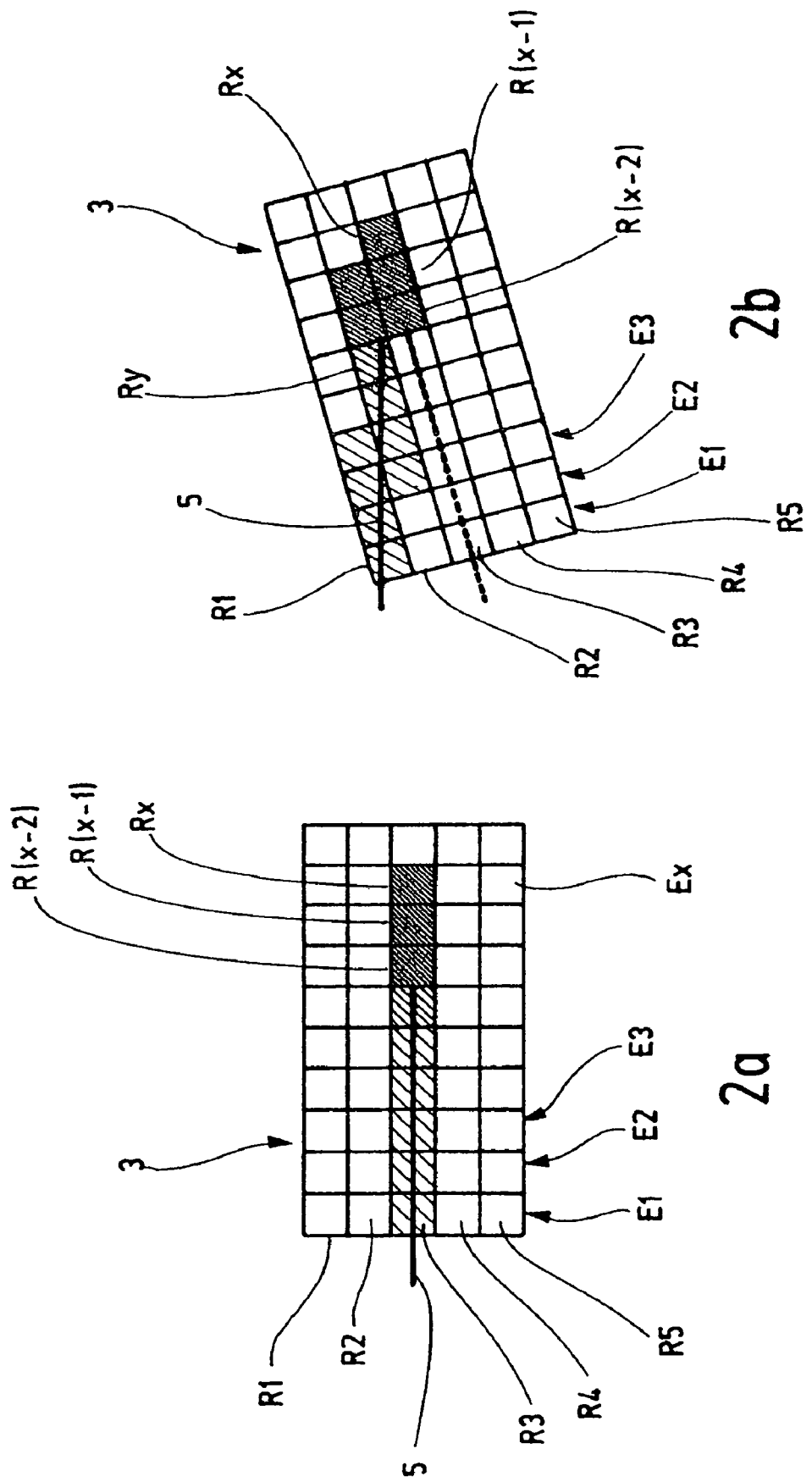

The invention is explained in further detail in the following with reference to the drawings in which:

FIG. 1 is a basic diagram of a device for the irradiation of tumour tissue in a patient and FIG. 2 is a basic diagram of a portion of a tumour to illustrate the effect of a movement on an irradiation operation.

FIG. 1 shows a basic diagram of a device 1 for the slice-by-slice irradiation of tumour tissue 3 using a particle beam 5, which is provided by an accelerator 7 that is merely outlined here. The accelerator supplies the particles with the energy required for the layer that is currently being irradiated. The particle beam 5 is deflected by means of a raster scanning device 9 in both horizontal direction and vertical direction in order to scan the tumour tissue 3 slice-by-slice. By way of example, the raster scanning device 9 is for that purpose provided here with a first pair of magnets 11 and a second pair of magnets 13. The slice to be irradiated is addressed by the particle energy delivered by the accelerator. The particles used are preferably $^{12}C$ particles.

The beam leaving the raster scanning device 9 runs through a particle counter 15, which can be formed, for example, as an ionisation chamber, then passes through a modulator 17 arranged down-beam and subsequently arrives at the tumour tissue 3 to be irradiated. As indicated by arrows 19, the latter is capable of moving.

The modulator 17 can have at least two modulator plates 21, 23 of wedge-shaped form lying opposite to one another, which can be moved towards and away from one another by means of a suitable drive, so that the particle beam 5 passes through a more or less thick modulator material before it strikes the tumour tissue 3. Preferably, the modulator 17 has a plurality of several plates 21, 21', 21" etc, lying adjacent to one another and modulator plates 23, 23', 23" etc. lying adjacent to one another, there being associated with each of the plates 21, 21' etc. lying adjacent to one another a first drive 25, and associated with each of the plates 23, 23' etc. lying adjacent to one another a second drive 27, which drives form part of a drive device 29. Modulators of that kind are known, so no further details about them are given here.

The energy of the particle beam 5 is modulated using the modulator 17, by which means the position of the Bragg maximum measured in the direction of the particle beam is varied, especially by which means the penetration depth is varied in such a manner that it remains in the desired layer even in the event of, for example, respiratory movements and the changes in density in the patient resulting therefrom.

By means of the raster scanning device 9 the tumour tissue 3 is thus scanned slice-by-slice, that is, is acted upon by particles of the particle beam. The modulator 17 serves to match the position of a scan slice measured in the direction of the particle beam 5 to the state of the respiratory movement.

In FIG. 1, a number of slices 3l, 3b etc. are indicated within the tumour tissue 3.

The dose of the particle beam 5 deposited in a region of the tumour depends on the number of particles present in the particle beam 5. During an irradiation operation, the number of particles acting on the tumour tissue 3 is determined by means of the particle counter 15. When the desired particle number is reached, a signal is delivered by a line 31 to a control means 33, which is connected via a line 35 to the raster scanning device 9. When the desired particle number is detected by the particle counter 15, activation of the raster scanning device 9 is effected via the line 35 in such a way that the next raster point within the tumour tissue 3 is addressed.

The device 1 also includes a detection device 37, and a module 39 which is connected via a line 41 to the detection device 37, via a line 43 to the modulator 17 and via a line 45 to the raster scanning device 9. Finally, the module 39 is connected via a line 47 to the particle counter 15.

Special preference is given to a device 1 that, for detecting the course of movement of tumour tissue, for example during a patient's breathing, has a detection device in the form of a fluoroscopy system or camera system.

FIG. 2 is a basic diagram of a portion of the tumour tissue 3, to the left, according to the numeral 2a, in a first position and to the right, according to the numeral 2b, in a second tilted position, for example on account of respiratory movements.

It is indicated by squares that the tumour tissue 3 is irradiated in grid form, planes E1, E2 and E3 etc. being shown in FIG. 2a. Squares present within a plane are intended to indicate individual raster points. The portion of tumour tissue in FIG. 2a shows the raster points R1 to R5.

It is evident from FIG. 2a that, by means of the particle beam 5, a raster point Rx in the plane Ex is acted upon by a dose. Raster points R(x−1), R(x−2) etc. to R3 lying to the left of the raster point Rx are at the same time already acted upon by a partial dose. At a raster point, therefore, not only is it the Bragg maxima located there that each contribute to the dose deposition, but also beams having Bragg maxima that lie deeper in the tissue.

FIG. 2b shows the partial element of the tumour tissue 3 in a position rotated anti-clockwise relative to FIG. 2a. The same reference numerals are used to indicate the same components that have already been illustrated in FIG. 2a. It is thus clear that the portion of tumour tissue 3 shown here has raster points arranged in planes E1, E2, E3 etc., the raster points R1 to R5 lying in the plane E1.

By modulation of the beam position, the particle beam 5 here strikes the raster point Rx again. Since the tumour tissue 3 is tilted, unlike in FIG. 2a the particle beam 5 does not pass through a row of raster points lying adjacent to one another but strikes raster points that lie in different rows. In the uppermost row of the portion of tumour tissue 3, four raster points lying adjacent to one another are struck, namely the raster point R1 and the three raster points adjacent thereto on the right. In the second row, raster points at a distance from the raster point R2 are struck, and finally raster points that lie in the same row as the raster point E3 lying in plane E1.

The raster point Ry is acted upon by a somewhat lower dose. The raster points lying to the left thereof are in turn irradiated with a lower dose.

It is evident from FIGS. 2a and 2b that in the irradiation of the raster point Rx by a particle beam, the Bragg maximum of the particle beam lying in Rx, differently arranged raster points are already being acted upon by a dose. The different relative positions of the raster points to one another are brought about by movement of the tumour, as illustrated here, for example, by degrees of rotation.

In the following, more detail is given on the operation of the device shown in FIG. 1 for the irradiation of tumour tissue in a patient and on the method of compensating for movements of a patient, or of the irradiated region of a patient, during an irradiation with a particle beam using a device according to FIG. 1.

During a movement, for example when the patient is breathing, the tumour tissue 3 of a patient is detected by means of a detection device, for example the detection device 37. The different positions of the tumour tissue 3 in the course of a movement can also be detected by breaking the movement down into quasi-static, preferably non-overlapping phases of movement. A time-resolved detection of movement of the tumour tissue thus occurs.

Prior to irradiation, the detection of movement is effected by means of a device that is preferably designed as a 4D-CT (4D computer tomograph). The movement phases generated therein can be detected indirectly, for example using a video camera that detects colour points on the skin of a patient or light sources applied thereto. During irradiation, the states of movement present can then, for example, be related to the movement phases of the 4D-CT. Preferably, though, the movement is detected by means of a detection device that is in the form of a fluoroscopy system or camera system for surface detection. The local position of the tumour tissue during an irradiation procedure can thus be determined continuously or at particular points in time.

Those data of the different movement phases are stored in a first storage device, not shown in FIG. 1.

During an irradiation operation, the movement of the tumour is related to the movement phases by the detection system. Correlation in a module 39 with the data from the first storage device is used to control the raster scanning device 9 and the modulator 17 so that the particle beam 7 irradiates the tumour tissue 3 in the different movement phases as planned.

Those data are thus used so to control the raster scanning device 9 that slice-by-slice scanning of the tumour tissue 3 occurs even during movement.

The penetration depth of the particle beam 5 in the tumour tissue, that is the plane 3a, 3b etc. within the tumour tissue 3 in which the Bragg maximum of the particle beam lies, is set by activation of the modulator 17, the modulator plates 21, 21', 21" and 23, 23', 23" etc. of which are moved towards one another to a greater or less extent by means of the drives 25 and 27.

During the irradiation of a raster point within the tumour tissue 3, the particle number of the particle beam 5 is determined by means of the particle counter 15, which, for example, is in the form of an ionisation chamber. When the desired particle number at a raster point is reached, the raster scanning device 9 is activated in such a manner that the next raster point is irradiated. During an irradiation operation, the current position of the patient, or of the tumour tissue 3, is detected in time-resolved manner using the detection device 37. It is possible for indirect detection, for example by means of a video camera, or direct detection, for example by way of a fluoroscopy system or camera system, to be carried out here.

On the one hand, the module 39 detects the irradiation operation currently in progress by detecting over time the current raster point within the tumour tissue 3 and the dosage radiated-in there. In that manner, which raster points of the tumour tissue 3 have been irradiated with what dose at which point in time are known exactly. Conversely, the dosage radiated-in per raster point that was reached by the irradiation operation can thus also be determined.

On the other hand, the movement of the tumour tissue 3 during the irradiation is determined by means of the module 39. As a result, it is known which actual raster point within the body of the patient has been acted upon by what dose at a particular point in time.

The data relating to the irradiation operation, and the movement of the tumour tissue 3 occurring during the irradiation operation, are correlated with one another in order to be able to determine the said information about the dose at a raster point in the body of the patient.

The information obtained by the correlation can be stored in a second storage device, which is not shown here. If the first storage device is appropriately formed, those data can also be stored therein. They deliver a protocol of an irradiation, which protocol can be evaluated after the irradiation. In that way it is possible to assess the irradiation results. For example, it is possible to ascertain whether and which raster points of a tumour have been irradiated with too low a dose.

As a rule, a plurality of treatment portions, also called fractions, are provided for the treatment of tumour tissue. Based on the data laid down in the protocol, the dose to be selected for the raster points of the tumour tissue in a subsequent irradiation can be determined anew.

Especially preferably, the information obtained by the correlation of the data of the module 39 can be used to intervene in an irradiation operation that is in progress: it is thus possible for the dose of particle beams 5 directed by a raster scanning device 9 onto a tumour tissue 3 to be adapted if the target area has moved. In an irradiation operation, the individual raster points of the tumour tissue are acted upon by a particle beam 5. Before irradiation of a further raster point, it is possible on the basis of the data present in the module 39 to determine the dose that is to be used for the next raster point. In so doing, it is possible to take into consideration whether that raster point has possibly already been acted upon by a partial dose during the irradiation of previous raster points (see FIG. 2). If that is the case, then the radiation dose for that previously irradiated raster point is adapted. Such an adaptation may result in an increase or, however, even a reduction in the dose to be applied. In such an arrangement of the device 1, the data relating to the irradiation operation present in the module 39 and the data relating to the movement of the patient are correlated, and the information obtained therefrom is used to influence the raster scanning device 9 and the modulator 17 directly.

Preferably, possible movement phases of the tumour tissue are detected and stored prior to an irradiation operation. Prior to introducing the particle beam 5 into a particular raster point of the tumour tissue, it is thus possible, by way of a correction value retrieved from a storage device, for the necessary correction of the beam position and setting of the modulator to be determined, as well as the dose for the next raster point.

By means of the connection of the module 39 to the raster scanning device 9 and to the modulator 17, a control circuit is formed that substantially improves the method of irradiating tumour tissue in a patient using a particle beam, because movements of the tumour tissue during an irradiation operation are compensated.

In the run-up to the irradiation of tumour tissue 3 in a patient using the device 1 described herein, processes for the dose calculation and for irradiation planning are carried out.

In the process for calculating the dose for the scanned particle beams, the different positions of the tumour tissue to be irradiated are detected in a patient. Accordingly, the course of movement of the tumour tissue 3 is ascertained in order later to be able to irradiate in a patient a tumour that is not static but moves during the irradiation operation, for example because of the patient's breathing.

The movement of the tumour tissue is divided up into quasi-static movement phases, which preferably do not overlap one another. The movement is accordingly not stored continuously but stored in relation to individual separate movement phases.

For each movement phase a partial-irradiation plan is set up, wherein the dose for a movement phase during which the tumour tissue 3 is scanned with a particle beam 5 is calculated from the partial-irradiation plan and the associated movement phase. For each movement phase, therefore, both a partial-irradiation plan and a partial dose are obtained.

The anatomical structures in the different movement phases do not, on account of the movement, always come to lie at exactly the same positions. The individual doses per movement phase, that is the partial doses, thus cannot easily be added up. It is necessary to convert the partial doses associated with the movement phases to a reference state taking into account the anatomical movements.

Only after that conversion is it possible to add up the partial doses to a total dose.

In order to be able to define the position of the Bragg maximum during an irradiation operation, it is necessary for the Bragg maximum to be converted from the reference state into other phases by means of a correction value. This is assured by a computer component not shown here.

In that procedure, it is necessary to take into account a first correction value, which results from the movement of the tumour tissue 3. In that case there is used as correction value a vector or a correction triplet, consisting of two lateral correction values for the beam tracking and a depth correction value, from which the required energy modulation is produced. In addition, in the determination of the correction value it is necessary to take into consideration, in the irradiation of another raster point, that individual raster points of the tumour tissue 3 have already been loaded by a partial dose. That dose contribution is different depending on the progress of the irradiation. For that case it is necessary for a pre-irradiation variable to be used as the correction value.

By means of the method described herein it is possible for the parameters for the particle beam that are associated with the reference state to be stored. In addition, a value table that contains the correction values on the one hand in relation to the movement and on the other hand in relation to the pre-irradiation are stored in a storage device.

The process, likewise connected in series before the actual irradiation, of irradiation planning for scanned particle beams for a device 1 for the irradiation of tumour tissue 3 in a patient using a particle beam 5, comprises the following steps:

As in the process for dose calculation, different positions of the tumour tissue in a patient are detected during the course of a movement, for example during the patient's breathing. The movement is in this process divided up into quasi-static, preferably non-overlapping movement phases.

In a further step, the anatomical position of the current raster point for a planned irradiation is ascertained from the combination of a raster point in the reference state with a state of movement that is related to the current raster point. Accordingly, for any combination of raster point and state of movement the anatomical position of the current raster point is tracked by way of the above-mentioned conversions.

Where a deviation of the current raster point compared with a raster point determined on the basis of the reference state exists, a correction value is calculated for the current raster point. That correction value is designated as a vector or as a correction triplet.

The correction values for each raster point, combined with each state of movement, are stored in a storage device in the form of a table. Also, for the sets of correction values there are stored in a storage device, for each raster point, the possible combinations with the states of movement. Thus, in an irradiation based on the irradiation plan ascertained here, the correction values can be applied on the basis of the then observed movement of the tumour tissue.

For each raster point the dose deposition of other raster points can be taken into consideration by taking into account all combinations of movement phases and raster point associations. From that a set of pre-irradiation variables can be determined for all possible courses of irradiation. In the process for irradiation planning, as also in the process for dose calculation, the anatomical position of the current raster point can be determined by means of a 4D-CT or a 4D-MR device (4D magnetic resonance device). The anatomical data are consequently available as time-resolved data.

Here, too, as described above with reference to the process for dose calculation, a conversion of the partial doses to a reference state is necessary before the partial doses can be added up.

The invention claimed is:

1. A method of dose calculation for scanned particle beams for a device for the irradiation with a particle beam of tumour tissue in a patient, the method comprising:
   detecting different positions of the tumour tissue during the course of a movement,
   dividing the movement into quasi-static movement phases that preferably do not overlap one another,
   establishing a partial-irradiation plan of a reference irradiation plan per movement phase, the dose for a movement phase being calculated from the partial-irradiation plan and the associated movement phase,
   converting, corresponding to the movement phase, partial doses associated with the movement phases to a reference state and
   adding the individual doses to a total dose.

2. A method of claim 1 wherein, during an irradiation, a Bragg maximum from the reference state is converted by means of a correction value into other phases.

3. A method of claim 1 wherein, as correction value there is/are used a vector or a correction triplet to compensate for the movement and/or a pre-irradiation variable taking into account the pre-irradiation.

* * * * *